United States Patent
Chen et al.

(10) Patent No.: US 10,465,190 B1
(45) Date of Patent: Nov. 5, 2019

(54) IN VITRO TRANSCRIPTION METHODS AND CONSTRUCTS

(71) Applicant: ModernaTX, Inc., Cambridge, MA (US)

(72) Inventors: Jesse Chen, Lexington, MA (US); Athanasios Dousis, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 90 days.

(21) Appl. No.: 15/387,263

(22) Filed: Dec. 21, 2016

Related U.S. Application Data

(60) Provisional application No. 62/387,320, filed on Dec. 23, 2015.

(51) Int. Cl.
*C07H 21/04* (2006.01)
*C12N 15/113* (2010.01)
*C12N 9/12* (2006.01)
*A61K 31/70* (2006.01)

(52) U.S. Cl.
CPC .......... *C12N 15/113* (2013.01); *C12N 9/1247* (2013.01); *C12N 2830/60* (2013.01); *C12N 2840/60* (2013.01)

(58) Field of Classification Search
CPC ................ C12N 15/113; C12N 9/1247; C12N 2840/60; C12N 2830/60
See application file for complete search history.

(56) References Cited

U.S. PATENT DOCUMENTS

| | | | |
|---|---|---|---|
| 7,335,471 B2 | 2/2008 | Guillerez et al. | |
| 8,710,200 B2 | 4/2014 | Schrum et al. | |
| 8,754,062 B2 | 6/2014 | De Fougerolles et al. | |
| 8,822,663 B2 | 9/2014 | Schrum et al. | |
| 8,999,380 B2 | 4/2015 | Bancel et al. | |
| 9,045,740 B2 * | 6/2015 | Martin .................. | C12N 9/127 |
| 9,221,891 B2 | 12/2015 | Bancel et al. | |
| 9,303,079 B2 | 4/2016 | Bancel et al. | |
| 9,464,124 B2 | 10/2016 | Bancel et al. | |
| 9,512,456 B2 | 12/2016 | Wang et al. | |
| 9,597,380 B2 | 3/2017 | Chakraborty et al. | |
| 9,868,691 B2 | 1/2018 | Benenato et al. | |
| 9,872,900 B2 | 1/2018 | Ciaramella et al. | |
| 10,064,934 B2 | 9/2018 | Ciaramella et al. | |
| 10,064,935 B2 | 9/2018 | Ciaramella et al. | |
| 10,124,055 B2 | 11/2018 | Ciaramella et al. | |
| 2007/0037245 A1* | 2/2007 | Endo .................... | C12P 21/005 435/68.1 |
| 2013/0102034 A1 | 4/2013 | Schrum et al. | |
| 2013/0259923 A1 | 10/2013 | Bancel et al. | |
| 2013/0266640 A1 | 10/2013 | De Fougerolles et al. | |
| 2014/0147432 A1 | 5/2014 | Bancel et al. | |
| 2014/0148502 A1 | 5/2014 | Bancel et al. | |
| 2014/0193482 A1 | 7/2014 | Bancel et al. | |
| 2014/0206752 A1 | 7/2014 | Afeyan et al. | |
| 2014/0378538 A1 | 12/2014 | Bancel | |
| 2015/0141499 A1 | 5/2015 | Bancel et al. | |
| 2015/0307542 A1 | 10/2015 | Roy et al. | |
| 2015/0315541 A1 | 11/2015 | Bancel et al. | |
| 2016/0024141 A1 | 1/2016 | Issa et al. | |
| 2016/0038612 A1 | 2/2016 | Hoge et al. | |
| 2016/0317647 A1 | 11/2016 | Ciaramella et al. | |
| 2018/0002393 A1 | 1/2018 | Bancel et al. | |
| 2018/0028664 A1 | 2/2018 | Besin et al. | |
| 2018/0237849 A1 | 8/2018 | Thompson | |
| 2018/0243230 A1 | 8/2018 | Smith | |
| 2018/0271970 A1 | 9/2018 | Ciaramella et al. | |
| 2018/0273977 A1 | 9/2018 | Mousavi et al. | |
| 2018/0280496 A1 | 10/2018 | Ciaramella et al. | |
| 2018/0289792 A1 | 10/2018 | Ciaramella et al. | |
| 2018/0303929 A1 | 10/2018 | Ciaramella et al. | |
| 2018/0311336 A1 | 11/2018 | Ciaramella et al. | |
| 2018/0318409 A1 | 11/2018 | Valiante et al. | |

FOREIGN PATENT DOCUMENTS

| | | |
|---|---|---|
| WO | WO 2016/164762 | 10/2016 |
| WO | WO 2016/201377 | 12/2016 |
| WO | WO 2017/015457 | 1/2017 |
| WO | WO 2017/020026 | 2/2017 |
| WO | WO 2017/062513 A1 | 4/2017 |
| WO | WO 2017/070601 A1 | 4/2017 |
| WO | WO 2017/201340 A1 | 11/2017 |
| WO | WO 2017/201342 A1 | 11/2017 |
| WO | WO 2017/201347 A1 | 11/2017 |
| WO | WO 2018/053209 A1 | 3/2018 |
| WO | WO 2018/075980 A1 | 4/2018 |

(Continued)

OTHER PUBLICATIONS

Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Mignone, F. et al., Untranslated regions of mRNAs. Genome Biol. 2002;3(3):REVIEWS0004. Epub Feb. 28, 2002. pp. 1-10.
U.S. Appl. No. 15/239,613, filed Aug. 17, 2016, Laska et al.
U.S. Appl. No. 16/036,318, filed Jul. 16, 2018, Ciaramella et al.
U.S. Appl. No. 16/048,154, filed Jul. 27, 2018, Ciaramella et al.
U.S. Appl. No. 16/144,394, filed Sep. 27, 2018, Ciaramella et al.
U.S. Appl. No. 90/014,167, filed Aug. 17, 2018, Ciaramella et al.
U.S. Appl. No. 15/748,773, filed Jan. 30, 2018, Ciaramella et al.
U.S. Appl. No. 15/155,986, filed May 16, 2016, Fritz.

(Continued)

*Primary Examiner* — Quang Nguyen

(74) *Attorney, Agent, or Firm* — Wolf, Greenfield & Sacks, P.C.

(57) ABSTRACT

The present disclosure provides, in some aspects, in vitro transcription systems (including, for example, nucleic acid constructs and polymerases), the use of which increases transcription efficiency while reducing the amount of truncated single-stranded ribonucleic acid transcript produced during an in vitro transcription reaction.

14 Claims, 8 Drawing Sheets

Specification includes a Sequence Listing.

(56) References Cited

FOREIGN PATENT DOCUMENTS

| | | |
|---|---|---|
| WO | WO 2018/081459 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A2 | 11/2018 |

OTHER PUBLICATIONS

U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 16/001,751, filed Jun. 6, 2018, Mousavi et al.
U.S. Appl. No. 15/156,249, filed May 16, 2016, Miracco.
U.S. Appl. No. 15/767,587, filed Apr. 11, 2018, Ciaramella.
U.S. Appl. No. 16/006,526, filed Jun. 12, 2018, Ciaramella.
U.S. Appl. No. 15/767,600, filed Apr. 11, 2018, Ciaramella et al.
U.S. Appl. No. 16/023,013, filed Jun. 29, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 15/136,386, filed Sep. 20, 2018, Ciaramella et al.
U.S. Appl. No. 15/674,591, filed Aug. 11, 2017, Ciaramella et al.
U.S. Appl. No. 16/136,503, filed Sep. 20, 2018, Ciaramella et al.
U.S. Appl. No. 15/746,286, filed Jan. 19, 2018, Ciaramella et al.
U.S. Appl. No. 16/009,811, filed Jun. 15, 2018, Ciaramella et al.
U.S. Appl. No. 16/009,848, filed Jun. 15, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 15/905,576, filed Feb. 26, 2018, Bancel et al.
U.S. Appl. No. 15/674,107, filed Aug. 10, 2017, Besin et al.
U.S. Appl. No. 15/674,872, filed Aug. 11, 2017, Besin et al.
U.S. Appl. No. 16/001,786, filed Jun. 6, 2018, Hoge et al.
U.S. Appl. No. 16/040,981, filed Jul. 20, 2018, Ciaramella et al.
U.S. Appl. No. 16/001,765, filed Jun. 6, 2018, Marquardt et al.
U.S. Appl. No. 15/880,436, filed Jan. 25, 2018, Ciaramella.
U.S. Appl. No. 16/001,951, filed Jul. 10, 2018, Ciaramella.
U.S. Appl. No. 16/302,607, filed Nov. 16, 2018, Benenato et al.
U.S. Appl. No. 16/131,793, filed Sep. 14, 2018, Ciaramella et al.
U.S. Appl. No. 16/180,076, filed Nov. 5, 2018, Cohen et al.

* cited by examiner

Full Sequence:
5'-CAG AAG C- 17nt promoter- 20nt ITS-AGA GTA AGA AGA AAT ATA AGA GCC ACC ATG GGA GTG CAC GAG TGT C-3' (SEQ ID NO: 1)

Fig. 4

Synthetic Template

5'-CAGAAGC TAA TAC GAC TCA CTA TA GGG AGA CCT CAT CTT TGA AG--27nt-ATG-16nt-3'

T7 Promoter — 20 nt ITS — T7 gene 9 — ORF 66 nt RNA transcript

Mutation at -16: 5'-GAT-3', 5'-TAT-3', 5'-CAT-3'
-15: 5'-AGT-3', 5'-ATT-3', 5'-ACT-3'
-14: 5'-AAG-3', 5'-AAC-3', 5'-AAA-3'

Mutation at 5'-ACC-3', 5'-ACG-3', 5'-AGG-3'
5'-CAC-3', 5'-CAG-3', 5'-GAG-3'
5'-CCT-3', 5'-CGT-3', 5'-GCT-3'
5'-CCG-3'

Consensus: 5'-AAT-3'

IN VITRO TRANSCRIPTION METHODS AND CONSTRUCTS

RELATED APPLICATIONS

This application claims the benefit under 35 U.S.C. § 119(e) of U.S. provisional application No. 62/387,320, filed Dec. 23, 2015, which is incorporated by reference herein in its entirety.

BACKGROUND

Abortive initiation is an early process of genetic transcription in which RNA polymerase binds to a DNA promoter and enters into cycles of synthesis of short (truncated) mRNA transcripts that are released before the transcription complex disassociates from the promotor. The truncated RNA transcripts cannot be converted to full-length transcripts by RNA polymerase and become by-product that accumulates during the course of transcription. This process occurs in both eukaryotes and prokaryotes. Abortive initiation is typically studied in the T3 and T7 RNA polymerases in bacteriophages and in *Escherichia coli*.

Abortive initiation is a normal process of transcription and occurs both in vitro and in vivo. After each nucleotide-addition step in initial transcription, RNA polymerase, stochastically, can proceed on the pathway toward promoter escape (productive initiation) or can release the RNA product (transcript) and revert to the RNA polymerase-promoter open complex (abortive initiation). During this early stage of transcription, RNA polymerase enters a phase during which dissociation of the transcription complex energetically competes with the elongation process.

SUMMARY

Provided herein, in some aspects, are nucleic acid constructs and modified polymerases, the use of which increases transcription efficiency while reducing the amount of truncated (e.g., 3-12 nucleotide (nt)) single-stranded ribonucleic acid (ssRNA) (e.g., mRNA) transcript produced during an in vitro transcription (IVT) reaction. In a typical IVT reaction, greater than 50% (molarity) of the RNA transcripts produced are truncated abortive products (referred to herein as truncated ssRNA transcripts). Only a small fraction (e.g., 0.2-0.5%) of initiation events lead to full-length "run-off" ssRNA transcripts, which is inefficient and costly for large-scale IVT RNA synthesis systems. Advantageously, use of the IVT systems of the present disclosure (which include, for example, nucleic acid constructs and/or modified polymerases), in some embodiments, results in a product (RNA transcript) ratio of less than 1:1 of truncated ssRNA transcript:full-length ssRNA transcript and/or a product yield that is at least 15 times (15-fold) greater than the starting template (DNA template).

Thus, some aspects of the present disclosure provide in vitro transcription constructs that comprise a modified T7 promoter operably linked to nucleic acid comprising a sequence that encodes a 5' untranslated region (UTR) and a sequence that encodes a RNA of interest, wherein the sequence that encodes the 5' UTR comprises a transcription start site and an initially transcribed sequence (ITS), and wherein the ratio of truncated single-stranded RNA (ssRNA) transcript:full-length ssRNA transcript produced from in vitro transcription of the construct is less than 1:1, and/or the amount of full-length single-stranded RNA produced from in vitro transcription of the construct is at least 15 times greater than the initial amount of the construct. In some embodiments, in vitro transcription of the construct results in a ratio of less than 1:1 of truncated single-stranded RNA (ssRNA) transcript:full-length ssRNA transcript. In some embodiments, the amount of full-length single-stranded RNA produced from in vitro transcription of the construct is at least 15 times greater than the initial amount of the construct.

Other aspects of the present disclosure provide in vitro transcription constructs that comprise a modified T7 promoter operably linked to nucleic acid comprising a sequence that encodes a 5' untranslated region (UTR), wherein the sequence that encodes the 5' UTR comprises a transcription start site and an initially transcribed sequence (ITS), and wherein the ratio of truncated single-stranded RNA (ssRNA) transcript:full-length ssRNA transcript produced from in vitro transcription of the construct linked to a sequence that encodes a RNA of interest is less than 1:1, and/or the amount of full-length single-stranded RNA produced from in vitro transcription of the construct linked to a sequence that encodes a RNA of interest is at least 15 times greater than the initial amount of the construct.

The present disclosure further provides, in some aspects, methods of producing a ribonucleic acid (RNA) of interest. The methods may comprise, for example, performing an in vitro transcription reaction using an in vitro transcription construct joined in-frame with a nucleic acid encoding a RNA of interest (e.g., mRNA), thereby producing a RNA of interest.

Also provided herein, in some aspects are methods that comprise delivering to a subject the RNA (e.g., mRNA) of interest produced by the methods of the present disclosure. In some embodiments, the RNA is formulated in a lipid nanoparticle prior to delivery. In some embodiments, a lipid nanoparticle comprises a cationic lipid, a PEG-modified lipid, a sterol and a non-cationic lipid.

In some embodiments, a modified T7 promoter comprises at least one modification at any one of positions −12 to −17 relative to the transcription start site. The modification may be, for example, a point mutation (single base modification). In some embodiments, a modified T7 promoter comprises at least two modifications (e.g., two to six, at least three, at least four or at least 5) at any positions between −12 to −17 relative to the transcription start site (e.g., the nucleotide directly adjacent to and downstream from the TATA box of the promoter, as discussed below).

In some embodiments, an initially transcribed sequence (ITS) has a length of 12 to 20 nucleotides, 12 to 15 nucleotides, or 15 to 20 nucleotides (e.g., 12, 13, 14, 15, 16, 17, 18, 19 or 20 nucleotides). In some embodiments, the ITS comprises a purine (A/G)-rich region. For example, at least (or equal to) 50% (e.g., 55%, 60% or 70%), or at least (or equal to) 75% (e.g., 75%, 80%, 85%, 90%, 95% or 98%), of the nucleotides of the ITS may be purines.

In some embodiments, an ITS is obtained from (or is derived from, or has identity, e.g., 100% identity, to) a gene of the T7 bacteriophage genome. For example, an ITS (e.g., having a length of 20 nucleotides) may be obtained from a gene selected from the group consisting of: Gene 1.1, Gene 1.3, Gene 1.5, Gene 1.6, Gene 2.5, Gene 3.8, Gene 4.2, Gene 4.3, Gene 4.7, Gene 6.5, Gene 9, Gene 10, Gene 13, Gene 17 and Gene 19.5 of the T7 genome. In some embodiments, an ITS shares at least (or equal to) 50% (e.g., 55%, 60% or 70%), or at least (or equal to) 75% (e.g., 75%, 80%, 85%, 90%, 95% or 98%) identity with a gene selected from the group consisting of: Gene 1.1, Gene 1.3, Gene 1.5, Gene 1.6, Gene 2.5, Gene 3.8, Gene 4.2, Gene 4.3, Gene 4.7, Gene 6.5, Gene 9, Gene 10, Gene 13, Gene 17 and Gene 19.5 of the T7 genome. In some embodiments, an ITS is identical to a sequence obtained from one of the foregoing T7 genes but for a single point mutation. In some embodiments, the ITS is identical to a sequence obtained from one of the foregoing T7 genes but for two to five (e.g., 2, 3, 4 or 5) point mutations.

In some embodiments, the ratio of truncated ssRNA transcript:full-length ssRNA transcript is 0.1:1 to 0.9:1 (e.g., 0.1:1 to 0.5:1).

In some embodiments, the amount of full-length single-stranded RNA produced from in vitro transcription of the construct is 15 times to 100 times (e.g., 15 times to 50 times) greater than the initial amount of the construct (or the initial amount of the DNA template).

In some embodiments, a RNA of interest (produced by a method as provided herein) is a messenger RNA (mRNA). In some embodiments, a RNA of interest (e.g., mRNA) is a therapeutic RNA, a prophylactic RNA, a diagnostic RNA, or a combination thereof. In some embodiments, the RNA (e.g., mRNA) encodes at least one (e.g., 1, 2, 3, 4, 5, 10 or 15) antigen.

Also provided herein, in some aspects, are in vitro transcription kits that comprise an in vitro transcription construct of the present disclosure and a T7 RNA polymerase comprising a modification in a C-linker region (e.g., amino acids 251 to 296) or a O-helix region of the polymerase.

In some embodiments, at least one modification in the C-linker region of the polymerase weakens the C-linker region by at least (or equal to) 10% (e.g., 10% to 90%, or 10%, 20%, 30%, 40%, 50%, 60%, 70%, 80% or 90%) relative to unmodified T7 RNA polymerase.

In some embodiments, at least one modification of the T7 RNA polymerase is selected from the group consisting of P266L, Q744L, Q744P, Y639F, H784A, E593G, Y639V, V685A, H784G, S430P, N433T, S633P, F849I and F880Y. In some embodiments, at least one modification includes Y639F and H784A. In some embodiments, at least one modification includes E593G, Y639V, V685A and H784G. In some embodiments, at least one modification includes S430P, N433T, S633P, F849I and F880Y. In some embodiments, at least one modification includes S430P, N433T, S633P, F849I , F880Y and P266L. In some embodiments, at least one modification includes S430P, N433T, S633P, F849I , F880Y, Y639F and H784A. In some embodiments, at least one modification includes S430P, N433T, S633P, F849I , F880Y, P266L, Y639F and H784A. In some embodiments, at least one modification includes S430P, N433T, S633P, F849I , F880Y, E593G, Y639V, V685A and H784G. In some embodiments, at least one modification includes S430P, N433T, S633P, F849I , F880Y, P266L, E593G, Y639V, V685A and H784G.

In some embodiments, at least one modification of the T7 RNA polymerase facilitates initiation-elongation transition. In some embodiments, at least one modification increases promoter clearance. In some embodiments, at least one modification increases stability and/or activity of the polymerase. In some embodiments, at least one modification at least one modification increases thermos stability of the polymerase. In some embodiments, at least one modification results in 2'-OMe incorporation.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the present disclosure.

FIG. 4 shows another example of synthetic IVT construct of the present disclosure (SEQ ID NO: 17) and associated modifications to the T7 promoter.

DESCRIPTION

Figure 1:
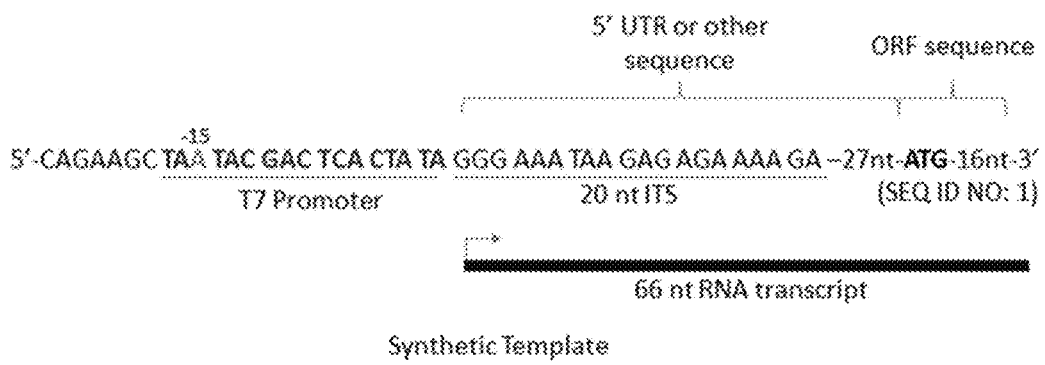
FIG. 1 shows an example of synthetic in vitro transcription (IVT) construct of the present disclosure (SEQ ID NO: 1).

The present disclosure provides, in some aspects, in vitro transcription systems (such as kits), including nucleic acid constructs and modified polymerases, the use of which increases transcription efficiency while reducing the amount of truncated single-stranded ribonucleic acid (ssRNA) (e.g., mRNA) transcript produced during an in vitro transcription (IVT) reaction. In some embodiments, the use of the IVT systems of the present disclosure results in a product (RNA transcript) ratio of less than 1:1 of truncated ssRNA transcript:full-length ssRNA transcript and/or a product yield that is at least 15 times (15-fold) greater than the starting template (DNA template, such as an IVT construct of the present disclosure).

Provided herein, in some aspects, are in vitro transcription (IVT) constructs having a modified promoter. A "promoter" refers to a control region of a nucleic acid at which initiation and rate of transcription of the remainder of a nucleic acid sequence are controlled. A promoter drives transcription of the nucleic acid sequence that it regulates, thus, it is typically located at or near the transcriptional start site of a gene. A promoter may have, for example, a length of 20 to 1000 nucleotides (e.g., 20-900, 20-800, 20-700, 20-600, 20-500, 20-400, 20-300, 20-200 or 20-100 nucleotides). A promoter may also contain sub-regions at which regulatory proteins and other molecules may bind, such as RNA polymerase and other transcription factors. For example, promoters typically have a TATA box, which is a conserved DNA sequence that indicates where a nucleotide (genetic) sequence can be read and decoded. A TATA box specifies to other molecules where transcription begins. In some embodiments, a "transcriptional start site" (the site at which transcription begins) of a construct of the present disclosure is located downstream and/or directly adjacent to the TATA box (or other most 3' sequence) of a promoter.

In some embodiments, a promoter is a T7 RNA promoter (a T7 promoter), which is recognized by T7 RNA polymerase (e.g., obtained from the T7 bacteriophage). T7 RNA polymerase (T7 polymerase) catalyzes the formation of RNA in the 5'→3' direction. T7 polymerase is highly promoter-specific (having an affinity of about 50 nM) and transcribes only DNA downstream of a T7 promoter (TAATACGACTCACTATA (SEQ ID NO: 18)), transcription beginning at the nucleotide directly adjacent to and downstream from the TATA box. Thus, in some embodiments, with reference to FIG. 1 as an example for the purpose of illustration, a "transcriptional start site" of a construct of the present disclosure refers to the G downstream (3') and directly adjacent to the TATA box of the T7 promoter. The T7 polymerase also requires a double stranded DNA template and $Mg^{2+}$ ion as a cofactor for the synthesis of RNA. T7 polymerase has a very low error rate and a molecular weight of 99 kDa.

A promoter is considered "modified" if it contains a nucleotide change (e.g., mutation, deletion, insertion or chemical modification) relative to its wild-type (unmodified) counterpart. For example, a T7 promoter having a C at position −15 is considered "modified" relative to a wild-type T7 promoter having an A at position −15 (see, e.g., FIG. 1). In some embodiments, a promoter (e.g., a T7 promoter) comprises at least one modification. For example, a promoter (e.g., a T7 promoter) may comprise 1 to 5 (e.g., 1, 2, 3, 4 or 5), or 1 to 10 (e.g., 1, 2, 3, 4, 5, 6, 7, 8, 9 or 10) modifications. In some embodiments, at least one modification of a promoter (e.g., a T7 promoter) is a point mutation. A point mutation may be a A→T, A→C, A→G, T→A, T→C, T→G, C→A, C→T, C→G, G→A, G→T, or a G→C mutation. Using the T7 promoter (SEQ ID NO: 18) as an example, at least one modification may be of any position between position −1 and position −17 (including position −1 and −17) relative to the 3' G. For example, at least one modification may be at position −1, −2, −3, −4, −5, −6, −7, −8, −9, −10, −11, −12, −13, −14, −15, −16 or −17. In some embodiments at least one modification of a T7 promoter is of a position between −12 and −17 (including −12 or −17). In some embodiments at least one modification of a T7 promoter is of a position between −14 and −16 (including −14 or −16).

In some embodiments, a modified T7 promoter comprises a T→A, T→C or T→G mutation at position −17. In some embodiments, a modified T7 promoter comprises a A→T, A→C or A→G mutation at position −16. In some embodiments, a modified T7 promoter comprises a A→T, A→C or A→G mutation at position −15. In some embodiments, a modified T7 promoter comprises a T→A, T→C or T→G mutation at position −14. In some embodiments, a modified T7 promoter comprises a A→T, A→C or A→G mutation at position −13. In some embodiments, a modified T7 promoter comprises a C→A, C→G or C→T mutation at position −12. In some embodiments, a modified T7 promoter comprises a G→A, G→C or G→T mutation at position −11. In some embodiments, a modified T7 promoter comprises a A→T, A→C or A→G mutation at position −10. In some embodiments, a modified T7 promoter comprises a C→A, C→G or C→T mutation at position −9. In some embodiments, a modified T7 promoter comprises a T→A, T→C or T→G mutation at position −8. In some embodiments, a modified T7 promoter comprises a C→A, C→G or C→T mutation at position −7. In some embodiments, a modified T7 promoter comprises a A→T, A→C or A→G mutation at position −6.

In some embodiments, a modified T7 promoter comprises a C→A, C→G or C→T mutation at position −5. In some embodiments, a modified T7 promoter comprises a T→A, T→C or T→G mutation at position −4. In some embodiments, a modified T7 promoter comprises a A→T, A→C or A→G mutation at position −3. In some embodiments, a modified T7 promoter comprises a T→A, T→C or T→G mutation at position −2. In some embodiments, a modified T7 promoter comprises a A→T, A→C or A→G mutation at position −1.

In some embodiments, a modified T7 promoter comprises at least one (e.g., 1, 2, 3, 4, 5 or 6) modification selected from the following: a T→A, T→C or T→G mutation at position −17; a A→T, A→C or A→G mutation at position −16; a A→T, A→C or A→G mutation at position −15; a T→A, T→C or T→G mutation at position −14; a A→T, A→C or A→G mutation at position −13; and a C→A, C→G or C→T mutation at position −12.

In some embodiments, a modified T7 promoter comprises at least one (e.g., 1, 2 or 3) modification selected from the following: a A→T, A→C or A→G mutation at position −16; a A→T, A→C or A→G mutation at position −15; and a T→A, T→C or T→G mutation at position −14.

Promoters are typically operably linked to a nucleic acid, or a sequence of a nucleic acid (nucleotide sequence). A promoter is considered to be "operably linked" to a sequence of nucleic acid that it regulates when the promoter is in a correct functional location and orientation relative to the sequence such that the promoter regulates (e.g., to control ("drive") transcriptional initiation and/or expression of) that sequence.

Provided herein, in some aspects, are in vitro transcription (IVT) constructs having a promoter operably linked to a nucleic acid comprising a sequence that encodes a 5' untranslated region (UTR). A 5' UTR is the region of an mRNA that is directly upstream (5') from an initiation (translation start) codon. A 5' UTR of the present disclosure may have a length of 20 to 100 nucleotides. For example, a 5' UTR may have a length of 20-100, 20-90, 20-80, 20-70, 20-60, 20-50, 20-40, 20-30, 25-100, 25-90, 25-80, 25-70, 25-60, 25-50, 25-40, 25-30, 30-100, 30-90, 30-80, 30-70, 30-60, 30-50, 30-40, 35-100, 35-90, 35-80, 35-70, 35-60, 35-50, 35-40, 40-100, 40-90, 40-80, 40-70, 40-60, 40-50, 45-100, 45-90, 45-80, 45-70, 45-60, 50-100, 50-90, 50-80, 50-70, 50-60, 55-100, 55-90, 55-80, 55-70, 60-100, 60-90, 60-80, 60- 70, 80-100, or 80-90 nucleotides. In some embodiments, a 5' UTR has a length of 20, 30, 40, 50, 60, 70, 80, 90 or 100 nucleotides. In some embodiments, a 5' UTR has a length of greater than 100 nucleotides.

In some embodiments, an IVT construct has a promoter operably linked to a nucleic acid comprising a sequence that encodes a 5' UTR. and a sequence that encodes a RNA of interest. A RNA of interest, in some embodiments, is a messenger RNA (mRNA). In some embodiments, a RNA of interest is a therapeutic RNA (e.g., mRNA), a prophylactic RNA (e.g., mRNA), or a diagnostic RNA (e.g., mRNA). A RNA of interest, in some embodiments, has an open reading frame encoding a (at least one) antigen. In some embodiments, a RNA of interest encodes an antigen obtained from an infectious agent, such as strains of bacteria or viruses.

In some embodiments, a RNA of interest is further chemically modified. The chemical modification may be selected from pseudouridine, N1-methylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine , 2-thio-dihydropseudouridine,    2-thio-dihydrouridine,    2-thiopseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, at least 80% of the uracil in the open reading frame of an RNA of interest have a chemical modification In some embodiments, the chemical modification is in the 5-position of the uracil.

In some embodiments, a RNA of interest is modified to comprise a (at least one) 5' terminal cap. For example, a RNA of interest may comprise a 7 mG(5')ppp(5')N1mpNp 5' terminal cap.

The sequence that encodes the 5' UTR comprises a transcriptional start site and an initially transcribed sequence. A "transcriptional start site" (the site at which transcription begins) is generally located downstream and/or directly adjacent to the TATA box of a promoter, as discussed above. A transcriptional start site, in some embodiments, defines the first nucleotide of an initially transcribed sequence (ITS). Thus, an ITS is the first region transcribed during an IVT reaction, for example. In some embodiments, an ITS has a length of 10-50 nucleotides. For example, an ITS may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, or 30-35 nucleotides. In some embodiments, an ITS has a length of 10, 11, 12, 13, 14, 15, 16, 17, 18, 19, 20, 21, 22, 23, 24, 25, 26, 27, 28, 29 or 30 nucleotides. In some embodiments, an ITS has a length of 12-20, 12-15 or 15-20 nucleotides. In some embodiments, an ITS has a length of 20 nucleotides, 20±5 nucleotides or 20±10 nucleotides.

In embodiments where an ITS is obtained from (or derived from, or synthesized based on) a wild-type, naturally-occurring or gene (e.g., a gene of the T7 genome), an ITS may be considered "modified" relative to its wild-type counterpart sequence. Various modifications are encompassed by the present disclosure. For example, an ITS may have a (at least one) point mutation relative to a wild-type counterpart sequence. A point mutation includes any nucleotide base change, for example, selected from the following: A→T, A→C, A→G, T→A, T→C, T→G, C→A, C→T, C→G, G→A, G→T, or G→C. In some embodiments, an ITS has 1-10, 1-9, 1-8, 1-7, 1-6, or 1-5 modifications relative to a wild-type counterpart sequence. For example, an ITS may have 1, 2, 3, 4, 5, 6, 7, 8, 9 or 10 modifications relative to a wild-type counterpart sequence.

In some embodiments, the ITS comprises a purine (A/G)-rich region. In some embodiments, at least 50% of the nucleotides of the ITS are purines. For example, at least 50%, at least 55%, at least 60%, at least 65%, at least 70%, at least 75%, at least 80%, at least 85%, at least 90%, at least 95% or 100% of the nucleotides of the ITS are purines. In some embodiments, 50%-100%, 50%-95%, 50%-90%, 50%-85%, 50%-80%, 50%-75%, 50-70%, 50%-65%, 50%-60%, 50%-55%, 55%-100%, 55%-95%, 55%-90%, 55%-85%, 55%-80%, 55%-75%, 55-70%, 55%-65%, 55%-60%, 60%-100%, 60%-95%, 60%-90%, 60%-85%,60%-80%, 60%-75%, 60-70%, 60%-65%, 65%-100%, 65%-95%, 65%-90%, 65%-85%, 65%-80%, 65%-75%, 65-70%, 70%-100%, 70%-95%, 70%-90%, 70%-85%, 70%-80%, 70%-75%, 75%-100%, 75%-95%, 75%-90%, 75%-85%, 75%-80%, 80%-100%, 80%-95%, 80%-90%, 80%-85%, 85%-100%, 85%-95%, 85%-90%, 90%-100%, 90%-95%, or 95%-100% of the nucleotides of the ITS are purines. In some embodiments, the ITS comprises a pyrimidine (T/C)-rich region.

In some embodiments, the ITS is obtained from a gene selected from the group consisting of Gene 1.1, Gene 1.3, Gene 1.5, Gene 1.6, Gene 2.5, Gene 3.8, Gene 4.2, Gene 4.3, Gene 4.7, Gene 6.5, Gene 9, Gene 10, Gene 13, Gene 17 and Gene 19.5 of the T7 genome. In some embodiments, an ITS is identical to (shares 100% identity with) a sequence obtained from one of the foregoing T7 genes and has a length of 20 nucleotides. In some embodiments, the ITS is modified relative to one of the genes of the T7 genome. In some embodiments, the ITS comprises at least one (e.g., at least 2, at least 3, at least 4) modification relative to the one of the genes of the T7 genome. In some embodiments, the ITS shares at least 50% identity with a gene selected from the group consisting of Gene 1.1, Gene 1.3, Gene 1.5, Gene 1.6, Gene 2.5, Gene 3.8, Gene 4.2, Gene 4.3, Gene 4.7, Gene 6.5, Gene 9, Gene 10, Gene 13, Gene 17 and Gene 19.5 of the T7 genome. For example, the ITS may share at least 55%, at least 60%, at least 65%, at least 70%, at least 75%, at least 80%, at least 85%, at least 90%, at least 95%, or greater identity with a gene obtained from the T7 genome. In some embodiments, the ITS shares 50%-95%, 50%-90%, 50%-85%, 50%-80%, 50%-75%, 50-70%, 50%-65%, 50%-60%, 50%-55%, 55%-95%, 55%-90%, 55%-85%, 55%-80%, 55%-75%, 55-70%, 55%-65%, 55%-60%, 60%-95%, 60%-85%,60%-80%, 60%-75%, 60-70%, 60%-65%, 65%-95%, 65%-90%, 65%-85%, 65%-80%, 65%-75%, 65-70%, 70%-95%, 70%-90%, 70%-85%, 70%-80%, 70%-75%, 75%-95%, 75%-90%, 75%-85%, 75%-80%, 80%-95%, 80%-90%, 80%-85%, 85%-95%, 85%-90%, 90%-95%, or greater identity with a gene obtained from the T7 genome. In some embodiments, an ITS is identical to a sequence obtained from one of the foregoing T7 genes. In some embodiments, an ITS has a length of 20 nucleotides and comprises at least one point mutation (e.g., 1, 2, 3, 4, 5, 6, 7, 8, 9, 10, 11, 12, 13, 14, 15, 16, 17, 18, 19 or 20 mutation(s)).

A rate limiting step during RNA transcription is the transition from the initiation state to the elongation state (0.008 s$^{-1}$), which is much slower than nucleotide addition (~0.4 s−1) or bond formation (~200 s$^{-1}$). Transcription with T7 polymerase produces a large amount of short abortive (truncated) ssRNA (e.g., 3-12 nt) product (e.g., >50% in molarity). Only a small fraction (e.g., 0.2-0.5%) of initiation events leads to full length (run-off) RNA products. T7 polymerase lacks proof-reading capability, and its error rate is estimated to be ~1x 10-4. There is a high error rate in A/T tract (e.g., 0.1-0.2%, referred to as transcriptional slippage). The RNA transcripts produced are predominantly N+1 and 3'-extension products (e.g., >70%).

The in vitro transcription constructs of the present disclosure, in some embodiments, reduce the amount of short abortive ssRNA transcript produced during in vitro transcription with T7 polymerase. Short abortive ssRNA transcript is referred to herein as "truncated ssRNA transcript." Truncated ssRNA transcript encompass ssRNA transcript having a length of 3-20 (e.g., 3, 4, 5, 6, 7, 8, 9, 10, 11, 12, 13, 14, 15, 16, 17, 18, 19 or 20) nucleotides. In some embodiments, truncated ssRNA transcript has a length of 3-7 nucleotides, 3-10 nucleotides, 3-12 nucleotides, or 3-15 nucleotides.

In some embodiments, the ratio of truncated single-stranded RNA (ssRNA) transcript:full-length ssRNA transcript produced from in vitro transcription of a construct (template) is less than 1:1. Thus, a T7 promoter of the constructs of the present disclosure may comprise a (at least one) modification that results in truncated ssRNA transcript: full-length ssRNA transcript production at a ratio of less than 1:1. In some embodiments, an ITS comprises a (at least one) modification relative to a wild-type counterpart sequence that results in truncated ssRNA transcript:full-length ssRNA transcript production at a ratio of less than 1:1. For example, the ratio of truncated ssRNA transcript: full-length ssRNA transcript produced from in vitro transcription of the construct may be less than 0.9:1, less than 0.8:1, less than 0.7:1, less than 0.6:1, less than 0.5:1, less than 0.4:1, less than 0.3:1 or less than 0.2:1. In some embodiments, the ratio of truncated ssRNA transcript:full-length ssRNA transcript produced from in vitro transcription of the construct is 0.1:1-0.9:1, 0.1:1-0.8:1, 0.1:1-0.7:1, 0.1:1-0.6:1, 0.1:1-0.5:1, 0.1:1-0.4:1, 0.1:1-0.3:1, 0.2:1-0.9:1, 0.2:1-0. 8:1, 0.2:1-0.7:1, 0.2:1-0.6:1, 0.2:1-0.5:1, 0.2:1-0.4: 1, 0.3:1-0.9:1, 0.3:1-0.8:1, 0.3:1-0.7:1, 0.3:1-0.6:1, 0.3:1-0.5:1, 0.4:1-0.9:1, 0.4:1-0.8:1, 0.4:1-0.7:1, 0.4:1-0.6:1, 0.5:1-0.9:1, 0.5:1-0.8:1, 0.5:1-0.7:1, 0.6:1-0.9:1, 0.6:1-0.8:1, or 0.7:1-0.9:1. In some embodiments, the ratio of truncated ssRNA transcript:full-length ssRNA transcript produced from in vitro transcription of the construct is 0.9:1, 0.8:1, 0.7:1, 0.6:1, 0.5:1, 0.4:1, 0.3:1, 0.2:1, or 0.1:1.

In some embodiments, the percentage of truncated ssRNA transcript produced from in vitro transcription of a construct is less than 50% of the total ssRNA transcript produced (including truncated and full-length RNA transcript). Thus, a T7 promoter of the constructs of the present disclosure may comprise a (at least one) modification that results in production of truncated ssRNA transcript in an amount that is less than 50% of the of truncated ssRNA transcript. In some embodiments, an ITS comprises a (at least one) modification relative to a wild-type counterpart sequence that results in production of truncated ssRNA transcript in an amount that is less than 50% of the of truncated ssRNA transcript. For example, the percentage of truncated ssRNA transcript produced from in vitro transcription of a construct may be less than 45%, less than 40%, less than 35%, less than 30%, less than 25%, less than 20%, less than 15%, less than 10%, less than 5%, or less than 2% of the total ssRNA transcript produced. In some embodiments, the percentage of truncated ssRNA transcript produced from in vitro transcription of a construct is 5%-45%, 5%-40%, 5%-35%, 5%-30%, 5%-25%, 5%-20%, 5%-15%, 5%-10%, 10%-45%, 10%-40%,10%-35%,10%-30%,10%-25%, 10%-20%,10%-15%, 15%-45%, 15%-40%,15%-35%,15%-30%,15%-25%, 15%-20%, 20%-45%, 20%-40%, 20%-35%, 20%-30%, 20%-25%, 25%-45%, 25%-40%, 25%-35%, 25%-30%, 30%-45%, 30%-40%, 30%-35%, 35%-45%, 35%-40%, or 40%-45% of the total ssRNA transcript produced. In some embodiments, the percentage of truncated ssRNA transcript produced from in vitro transcription of a construct is 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total ssRNA transcript produced.

The in vitro transcription constructs of the present disclosure, in some embodiments, increase the amount of full-length ssRNA construct produced during an in vitro transcription reaction. In some embodiments, the amount (e.g., µM) of full-length ssRNA produced from an in vitro transcription of a construct is at least 15 times (15-fold) greater than the initial amount of the construct (the amount of construct present in a reaction before transcription begins) (e.g., for an IVT reaction at 37° C. for 30 minutes using 0.2 µM construct and 0.1 µM T7 polymerase). Thus, a T7 promoter of the constructs of the present disclosure may comprise a (at least one) modification that results in production full-length ssRNA transcript in an amount that is at least 15 times greater than the amount of the initial construct. In some embodiments, an ITS comprises a (at least one) modification relative to a wild-type counterpart sequence that results in production full-length ssRNA transcript in an amount that is at least 15 times greater than the amount of the initial construct. For example, the amount (e.g., µM) of full-length ssRNA produced from an in vitro transcription of a construct may be at least 20 times, at least 30 times, at least 40 times, at least 50 times, at least 60 times, at least 70 times, at least 80 times, or at least 90 times greater than the initial amount of the construct. In some embodiments, the amount (e.g., µM) of full-length ssRNA produced from an in vitro transcription of a construct may be 100 times (100-fold) greater than the initial amount of the construct. In some embodiments, the amount (e.g., µM) of full-length ssRNA produced from an in vitro transcription of a construct is 15-100, 15-95, 15-90, 15-85, 15-80, 15-75, 15-70, 15-65, 15-60, 15-55, 15-50, 15-45, 15-40, 15-35, 15-30, 15-25,15-20, 20-100, 20-95, 20-90, 20-85, 20-80, 20-75, 20-70, 20-65, 20-60, 20-55, 20-50, 20-45, 20-40, 20-35, 20-30, 20-25, 25-100, 25-95, 25-90, 25-85, 25-80, 25-75, 25-70, 25-65, 25-60, 25-55, 25-50, 25-45, 25-40, 25-35, 25-30, 30-100, 30-95, 30-90, 30-85, 30-80, 30-75, 30-70, 30-65, 30-60, 30-55, 30-50, 30-45, 30-40, 30-35, 35-100, 35-95, 35-90, 35-85, 35-80, 35-75, 35-70, 35-65, 35-60, 35-55, 35-50, 35-45, 35-40, 40-100, 40-95, 40-90, 40-85, 40-80, 40-75, 40-70, 40-65, 40-60, 40-55, 40-50, 40-45, 45-100, 45-95, 45-90, 45-85, 45-80, 45-75, 45-70, 45-65, 45-60, 45-55, 45-50, 50-100, 50-95, 50-90, 50-85, 50-80, 50-75, 50-70, 50-65, 50-60, 50-55, 55-100, 55-95, 55-90, 55-85, 55-80, 55-75, 55-70, 55-65, 55-60, 60-100, 60-95, 60-90, 60-85, 60-80, 60-75, 60-70, 60-65, 65-100, 65-95, 65-90, 65-85, 65-80, 65-75, 65-70, 70-100, 70-95, 70-90, 70-85, 70-80, 70-75, 75-100, 75-95, 75-90, 75-85, 75-80, 80-100, 80-95, 80-90, 80-85, 85-100, 85-95, 85-90, 90-100, 90-95, or 95-100 times greater than the initial amount of the construct. In some embodiments, the amount (e.g., µM) of full-length ssRNA produced from an in vitro transcription of construct is greater than 100 times the initial amount of the construct. In some embodiments, the amount (e.g., µM) of full-length ssRNA produced from an in vitro transcription of a construct is 15, 20, 25, 30, 35, 40, 45, 50, 55, 60, 65, 70, 75, 80, 85, 90, 95, 100, 500 or 1000 times greater than the initial amount of the construct.

Also provided herein are modified polymerases (e.g., modified T7 RNA polymerases). When used in an IVT reaction in combination with a construct of the present disclosure, for example, the ratio of truncated ssRNA transcript:full-length ssRNA transcript may less than 1:1. For example, the ratio of truncated ssRNA transcript:full-length ssRNA transcript produced from in vitro transcription of a construct of the present disclosure in combination with a modified T7 polymerase may be less than 0.9:1, less than 0.8:1, less than 0.7:1, less than 0.6:1, less than 0.5:1, less than 0.4:1, less than 0.3:1 or less than 0.2:1. In some embodiments, the ratio of truncated ssRNA transcript:full-length ssRNA transcript produced from in vitro transcription of the construct is 0.1:1-0.9:1, 0.1:1-0.8:1, 0.1:1-0.7:1, 0.1:1-0.6:1, 0.1:1-0.5:1, 0.1:1-0.4:1, 0.1:1-0.3:1, 0.2:1-0.9:1, 0.2:1-0. 8:1, 0.2:1-0.7:1, 0.2:1-0.6:1, 0.2:1-0.5:1, 0.2:1-0.4: 1, 0.3:1-0.9:1, 0.3:1-0.8:1, 0.3:1-0.7:1, 0.3:1-0.6:1, 0.3:1-0.5:1, 0.4:1-0.9:1, 0.4:1-0.8:1, 0.4:1-0.7:1, 0.4:1-0.6:1, 0.5:1-0.9:1, 0.5:1-0.8:1, 0.5:1-0.7:1, 0.6:1-0.9:1, 0.6:1-0.8:1, or 0.7:1-0.9:1. In some embodiments, the ratio of truncated ssRNA transcript:full-length ssRNA transcript produced from in vitro transcription of the construct is 0.9:1, 0.8:1, 0.7:1, 0.6:1, 0.5:1, 0.4:1, 0.3:1, 0.2:1, or 0.1:1.

In some embodiments, when a modified T7 polymerase is used in an IVT reaction in combination with a construct of the present disclosure, the amount of full-length ssRNA produced is at least 15 times greater than the initial amount of the construct. For example, the amount (e.g., µM) of full-length ssRNA produced from an in vitro transcription of a construct of the present disclosure in combination with a modified T7 polymerase may be at least 20 times, at least 30 times, at least 40 times, at least 50 times, at least 60 times, at least 70 times, at least 80 times, or at least 90 times greater than the initial amount of the construct. In some embodiments, the amount (e.g., µM) of full-length ssRNA produced from an in vitro transcription of a construct may be 100 times (100-fold) greater than the initial amount of the construct. In some embodiments, the amount (e.g., µM) of full-length ssRNA produced from an in vitro transcription of a construct is 15-100, 15-95, 15-90, 15-85, 15-80, 15-75, 15-70, 15-65, 15-60, 15-55, 15-50, 15-45, 15-40, 15-35, 15-30, 15-25, 15-20, 20-100, 20-95, 20-90, 20-85, 20-80, 20-75, 20-70, 20-65, 20-60, 20-55, 20-50, 20-45, 20-40, 20-35, 20-30, 20-25, 25-100, 25-95, 25-90, 25-85, 25-80, 25-75, 25-70, 25-65, 25-60, 25-55, 25-50, 25-45, 25-40, 25-35, 25-30, 30-100, 30-95, 30-90, 30-85, 30-80, 30-75, 30-70, 30-65, 30-60, 30-55, 30-50, 30-45, 30-40, 30-35, 35-100, 35-95, 35-90, 35-85, 35-80, 35-75, 35-70, 35-65, 35-60, 35-55, 35-50, 35-45, 35-40, 40-100, 40-95, 40-90, 40-85, 40-80, 40-75, 40-70, 40-65, 40-60, 40-55, 40-50, 40-45, 45-100, 45-95, 45-90, 45-85, 45-80, 45-75, 45-70, 45-65, 45-60, 45-55, 45-50, 50-100, 50-95, 50-90, 50-85, 50-80, 50-75, 50-70, 50-65, 50-60, 50-55, 55-100, 55-95, 55-90, 55-85, 55-80, 55-75, 55-70, 55-65, 55-60, 60-100, 60-95, 60-90, 60-85, 60-80, 60-75, 60-70, 60-65, 65-100, 65-95, 65-90, 65-85, 65-80, 65-75, 65-70, 70-100, 70-95, 70-90, 70-85, 70-80, 70-75, 75-100, 75-95, 75-90, 75-85, 75-80, 80-100, 80-95, 80-90, 80-85, 85-100, 85-95, 85-90, 90-100, 90-95, or 95-100 times greater than the initial amount of the construct.

Polymerases (e.g., T7 polymerases) as provided herein may comprise a modification in a C-linker region of the polymerase. The C-linker region of the T7 polymerase, for example, includes amino acids 251-296 of the polymerase. In some embodiments, at least one modification in the C-linker region of the polymerase (e.g., T7 polymerase) weakens (e.g., destabilizes) the C-linker region by at least 10% relative to unmodified corresponding polymerase (e.g., unmodified T7 polymerase). In some embodiments, at least one modification in the C-linker region of a T7 polymerase weakens the C-linker region by 10-100%, 10-90%, 10-80%, 10-70%, 10-60%, 10-50%, 10-40%, 10-30% or 10-20% relative to unmodified corresponding unmodified T7 polymerase. In some embodiments, at least one modification in the C-linker region of a T7 polymerase weakens the C-linker region by 10%, 15%, 20%, 25%, 30%, 35%, 40%, 45%, 50%, 55%, 60%, 65%, 70%, 75%, 80%, 85%, 90%, 90%, 100%, or more, relative to unmodified corresponding unmodified T7 polymerase.

Polymerases (e.g., T7 polymerases) as provided herein may comprise a modification in a region of the polymerase that alters (e.g., weakens) interaction between the C-linker region and surrounding secondary structures. In some embodiments, the modification is in an O-helix region of the polymerase.

In some embodiments, at least one modification of a T7 polymerase is selected from P266L, Q744L, Q744P, Y639F, H784A, E593G, Y639V, V685A, H784G, S430P, N433T, S633P, F849I and F880Y. In some embodiments, the at least one modification includes Y639F and H784A. In some embodiments, the at least one modification includes E593G, Y639V, V685A and H784G. In some embodiments, the at least one modification includes S430P, N433T, S633P, F849I and F880Y. In some embodiments, the at least one modification includes S430P, N433T, S633P, F849I, F880Y and P266L. In some embodiments, the at least one modification includes S430P, N433T, S633P, F849I, F880Y, Y639F and H784A. In some embodiments, the at least one modification includes S430P, N433T, S633P, F849I, F880Y, P266L, Y639F and H784A. In some embodiments, the at least one modification includes S430P, N433T, S633P, F849I, F880Y, E593G, Y639V, V685A and H784G. In some embodiments, the at least one modification includes S430P, N433T, S633P, F849I, F880Y, P266L, E593G, Y639V, V685A and H784G.

In some embodiments, at least one modification of a T7 polymerase facilitates initiation-elongation transition.

In some embodiments, at least one modification of a T7 polymerase increases promoter clearance. For example, the at least one modification may increase promoter clearance by at least 10%, at least 15%, at least 20%, at least 25%, at least 30%, at least 35%, at least 40%, at least 45%, at least 50%, at least 75%, at least 100% or more relative to promoter clearance by an unmodified T7 polymerase. Promoter clearance may refer to any process involved in the transition from the initiation to the elongation phases of transcription by RNA polymerase, generally including a conformational change from the initiation conformation to the elongation conformation. Promoter clearance often involves breaking contact with transcription factors involved only in the initiation phase and making contacts with elongation specific factors.

In some embodiments, the at least one modification of a T7 polymerase increases stability and/or activity of the polymerase.

In some embodiments, the at least one modification of a T7 polymerase increases thermostability of the polymerase.

In some embodiments, the at least one modification of a T7 polymerase at least one modification results in 2'-OMe incorporation.

Also provided herein are in vitro transcription kits that include, for example, an in vitro transcription construct of the present disclosure and a polymerase (e.g., a T7 polymerase) comprising a modification in a C-linker region of the polymerase. Kits may further comprise ribonucleotide triphosphates and/or a buffer system (e.g., comprising dithiothreitol (DTT) and magnesium ions).

Also provided herein are methods of producing a RNA (e.g., mRNA) of interest, the method comprising performing an in vitro transcription reaction using the in vitro transcription construct of the present disclosure, thereby producing a RNA of interest.

Further provided herein are methods that comprise delivering to a subject the RNA of interest produced by any of the above methods. In some embodiments, the RNA is formulated in a lipid nanoparticle. In some embodiments, the lipid nanoparticle comprises a cationic lipid, a PEG-modified lipid, a sterol and a non-cationic lipid.

The present disclosure is further illustrated by the following Examples, which in no way should be construed as further limiting. The entire contents of all of the references (including literature references, issued patents, published patent applications, and co pending patent applications) cited throughout this application are hereby expressly incorporated by reference, in particular for the teachings that are referenced herein.

EXAMPLES

Examples 1-3 below evaluate the effects on in vitro transcription efficiency of modified T7 promoters, an initially transcribed sequences (ITSs) and modified T7 polymerases, respectively. FIG. 1 depicts the basic components of an in vitro transcription construct of the present disclosure, which includes a modified T7 promoter operably linked to nucleic acid comprising a sequence that encodes a 5' untranslated region (UTR) and a sequence that encodes a RNA of interest. The sequence that encodes the 5' UTR comprises a transcription start site (e.g., the "G" following the "TATA" box sequence of the T7 promoter) and an initially transcribed sequence (ITS) (e.g., first ~20 nucleotides of the 5' UTR).

The following conditions were used for the in vitro transcription reactions describe below: 100 nM wild-type (WT) T7 polymerase, 100 nM modified (P266L) T7 polymerase; 200 nM template/construct; 0.25 uCi/µL alpha-P32-GTP; 1 mM NTP; 0.01 U/µL IPPase; 2 U/µL RNaseOUT™ in 1x NEB T7 buffer; 37° C. for 30 min for WT T7 polymerase, or 1 hour for modified (P266L) T7 polymerase. Sequencing polyacrylamide gel electrophoresis (PAGE) analysis was performed using 20% acrylamide/Bis (19:1) gels with 7.5 M urea, 40 W for 2 hours. A Storage PhosphorImager Screen, Typhoon FLA 9500 was used for imaging and quantitation.

Figure 2:
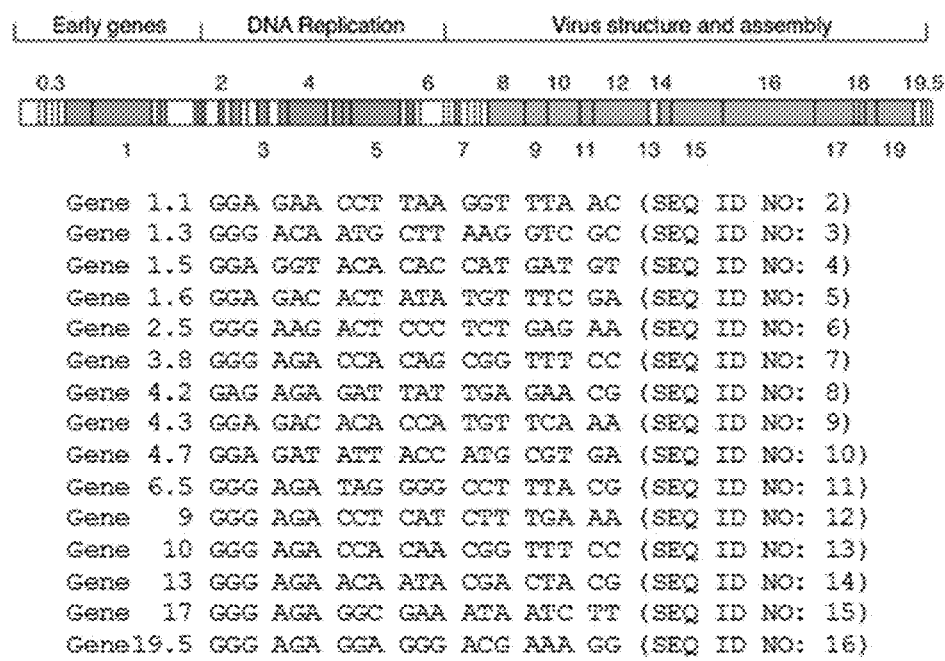
FIG. 2 shows initially transcribed sequences (ITSs) obtained from the T7 bacteriophage genome (SEQ ID NO: 2-16, top to bottom).
Figures 3A, 3B, 3C:
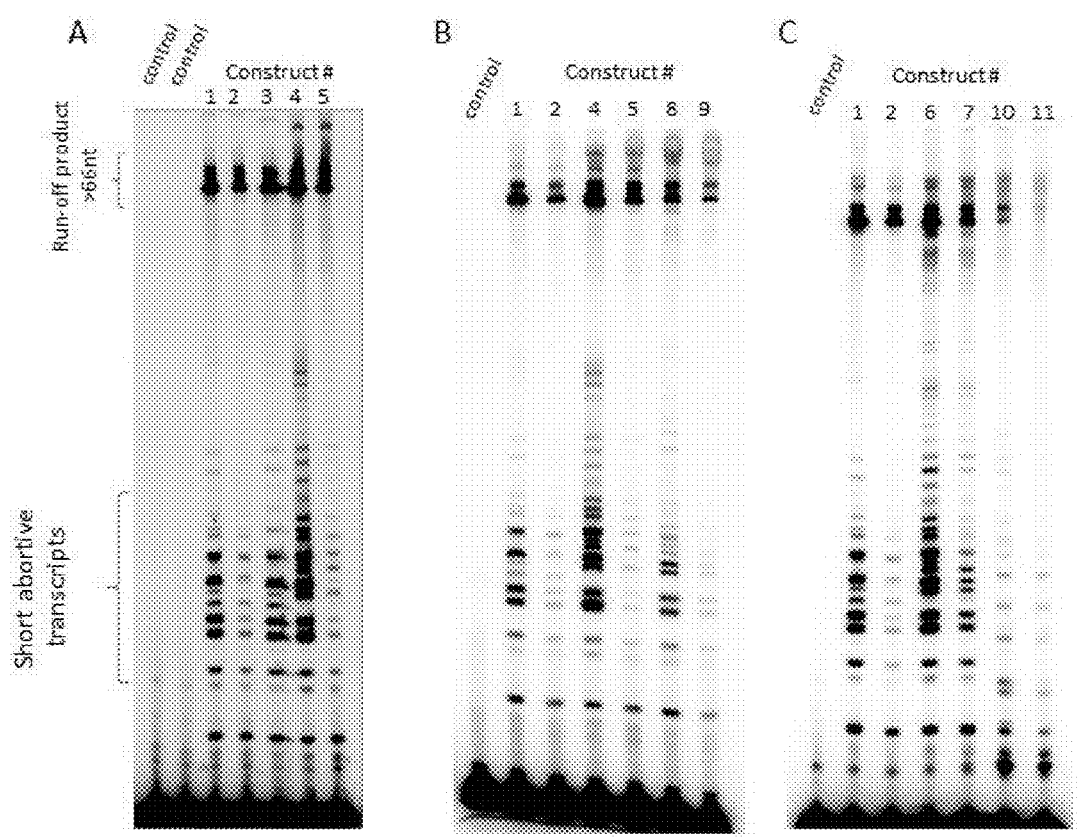
FIGS. 3A-3C show electrophoretic urea-polyacrylamide sequencing gel images of IVT transcripts produced in a reaction using the constructs (#1-#11) listed in Table 1 (C1 and C2 are controls).

Example 1: Effect of Initially Transcribed Sequences on In Vitro Transcription Efficiency In vitro transcription (IVT) reactions were performed using one of the eleven different constructs listed in Table 1. Constructs included a combination of a wild-type or modified (A-15C) T7 promoter with one of several different initially transcribed sequences (ITSs) (see, e.g., FIG. 2). Table 2 and FIGS. 3A-3C show results from the IVT reactions.

TABLE 2

| Template | Template | Abortive: Run-off | Run-off Product (µM) | % GTP consumed |
|---|---|---|---|---|
| 1 | 5UTR0 | 0.91:1 | 2.1 | 8.5 |
| 2 | 5UTR0$^{A/C}$ | 0.46:1 | 1.1 | 4.1 |
| 3 | 5UTR1 | 0.91:1 | 2.0 | 8.3 |
| 4 | Gene9 | 1.2:1 | 4.1 | 18 |
| 5 | Gene9$^{A/C}$ | 0.26:1 | 2.2 | 6.5 |
| 6 | Gene10 | 2.17:1 | 2.0 | 13.5 |
| 7 | Gene10$^{A/C}$ | 1.36:1 | 1.0 | 4.7 |
| 8 | Gene19.5 | 1.0:1 | 1.5 | 7.8 |
| 9 | Gene19.5$^{A/C}$ | 0.66:1 | 0.9 | 4.0 |
| 10 | C62 | 2.92:1 | 0.4 | 3.0 |
| 11 | C62$^{A/C}$ | 3.73:1 | 0.2 | 1.4 |

Example 2: Effect of Promoter Mutations on In Vitro Transcription Efficiency

Figure 5A:
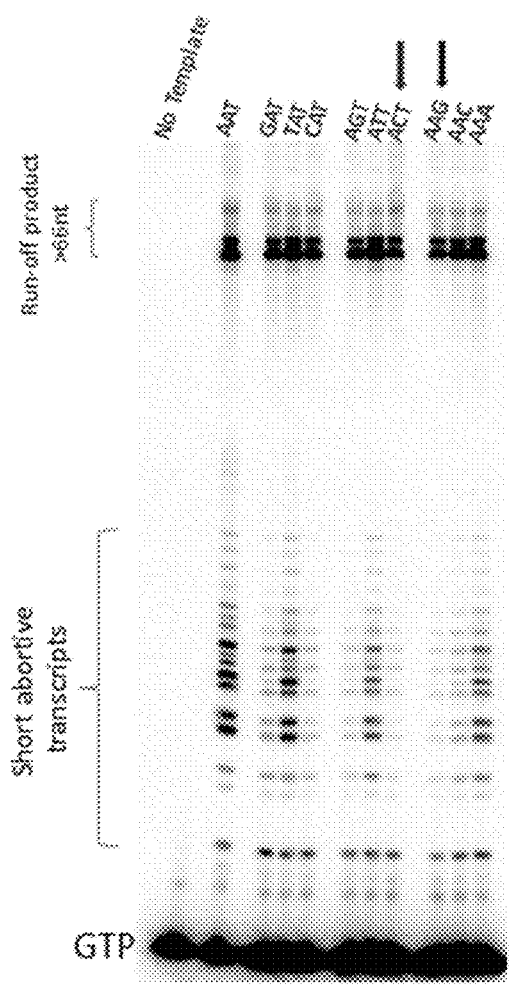
FIG. 5A shows an electrophoretic urea-polyacrylamide sequencing gel image of IVT transcripts produced in a reaction using constructs containing one of three different points mutation in the −14, −15 or −16 position of the T7 promoter (see FIG. 4). "AAT" is the consensus sequence. Better suppression of truncated ssRNA transcripts (abortive transcripts) was observed for AT→GC mutations relative to AT→TA at each position tested.
Figure 5B:
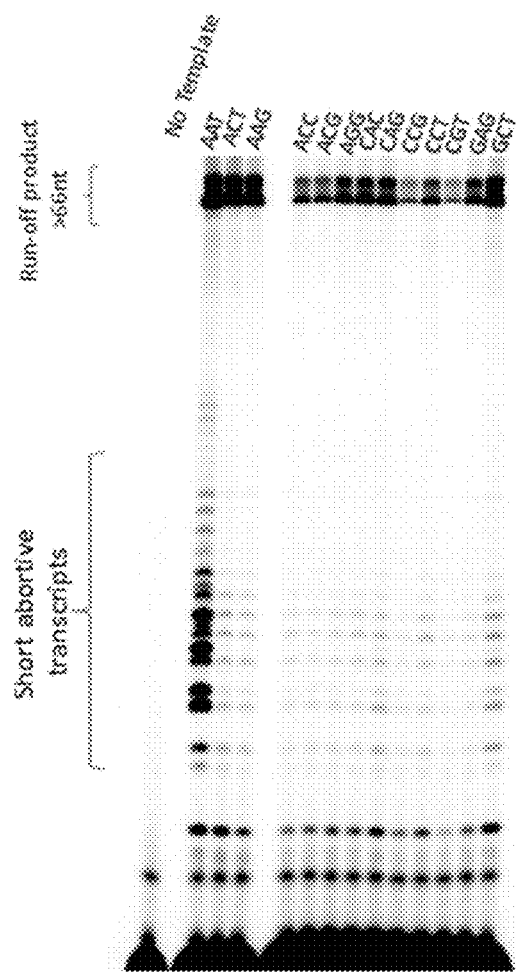
FIG. 5B shows an electrophoretic urea-polyacrylamide sequencing gel image images of IVT transcripts produced in a reaction using constructs containing double or triple mutations in the −14 to −16 region of the T7 promoter (see FIG. 4).

In vitro transcription (IVT) reactions were performed using one of 20 different constructs, each having a different modified T7 promoter (see Table 3, column 1, and FIG. 4) and an ITS obtained from T7 Gene 9. Table 3 and FIGS. 5A-5B shows results from the IVT reactions. Better suppression of truncated ssRNA transcripts (abortive transcripts) was observed for AT→GC mutations relative to AT→TA at each position tested (compare, e.g., lanes highlighted by arrows in FIG. 5A).

TABLE 1

| Construct Number | Template Name | Sequences |
|---|---|---|
| 1 | 5UTR0 | 5'-CAGAAGC TAATACGACTCAC TATAGGGAA ATAAG AGAGA AAAGA-46nt-3' (SEQ ID NO: 19) |
| 2 | 5UTR0$^{A/C}$ | 5'-CAGAAGC TACTACGACTCAC TATAGGGAA ATAAG AGAGA AAAGA-46nt-3' (SEQ ID NO: 20) |
| 3 | 5UTR1 | 5'-CAGAAGC TAATACGACTCAC TATAGGGAA AGAAGAGAGAA AAGA-46nt-3' (SEQ ID NO: 21) |
| 4 | Gene9 | 5'-CAGAAGC TAATACGACTCAC TATAGGGAG ACCTC ATCTT TGAAG-46nt-3' (SEQ ID NO: 22) |
| 5 | Gene9$^{A/C}$ | 5'-CAGAAGC TACTACGACTCAC TATAGGGAG ACCTC ATCTT TGAAG-46nt-3' (SEQ ID NO: 23) |
| 6 | Gene10 | 5'-CAGAAGC TAATACGACTCAC TATA GGGAG ACCAC AACGG TTTCC-46nt-3' (SEQ ID NO: 24) |
| 7 | Gene10$^{A/C}$ | 5'-CAGAAGC TACTACGACTCAC TATA GGGAG ACCAC AACGG TTTCC-46nt-3' (SEQ ID NO: 25) |
| 8 | Gene19.5 | 5'-CAGAAGC TAATACGACTCAC TATA GGGAG AGGAG GGACG AAAGG-46nt-3' (SEQ ID NO: 26) |
| 9 | Gene19.5$^{A/C}$ | 5'-CAGAAGC TACTACGACTCAC TATA GGGAG AGGAG GGACG AAAGG-46nt-3' (SEQ ID NO: 27) |
| 10 | C62* | 5'-CAGAAGC TAATACGACTCAC AATC GCGGA GCCTC ATCTT TGAAG-46nt-3' (SEQ ID NO: 28) |
| 11 | C62$^{A/C}$ | 5'-CAGAAGC TACTACGACTCAC AATC GCGGA GCCTC ATCTT TGAAG-46nt-3' (SEQ ID NO: 29) |

TABLE 3

| Promoter | Abortive: Run-off | Run-off Product (μM) | % GTP Consumption |
|---|---|---|---|
| 5'-AAT-3' | 0.87:1 | 7.3 | 27.1 |
| 5'-GAT-3' | 0.33:1 | 4.3 | 11.6 |
| 5'-TAT-3' | 0.62:1 | 5.6 | 18.3 |
| 5'-CAT-3' | 0.27:1 | 3.9 | 10.0 |
| 5'-AGT-3' | 0.23:1 | 3.4 | 8.2 |
| 5'-ATT-3' | 0.38:1 | 5.8 | 16.1 |
| 5'-ACT-3' | 0.19:1 | 3.6 | 8.4 |
| 5'-AAG-3' | 0.16:1 | 3.5 | 8.0 |
| 5'-AAC-3' | 0.24:1 | 4.4 | 11.0 |
| 5'-AAA-3' | 0.54:1 | 5.0 | 15.5 |
| 5'-ACC-3' | 0.35:1 | 0.7 | 2.0 |
| 5'-ACG-3' | 0.42:1 | 0.8 | 2.2 |
| 5'-AGG-3' | 0.33:1 | 1.2 | 3.1 |
| 5'-CAC-3' | 0.32:1 | 1.3 | 3.5 |
| 5'-CAG-3' | 0.49:1 | 1.4 | 4.2 |
| 5'-CCG-3' | 0.55:1 | 0.5 | 1.6 |
| 5'-CCT-3' | 0.51:1 | 0.9 | 2.7 |
| 5'-CGT-3' | 0.36:1 | 0.4 | 1.2 |
| 5'-GAG-3' | 0.29:1 | 1.1 | 2.7 |
| 5'-GCT-3' | 0.36:1 | 2.8 | 7.6 |

Example 3: Effect of Polymerase Mutations on In Vitro Transcription Efficiency

Figure 6A:
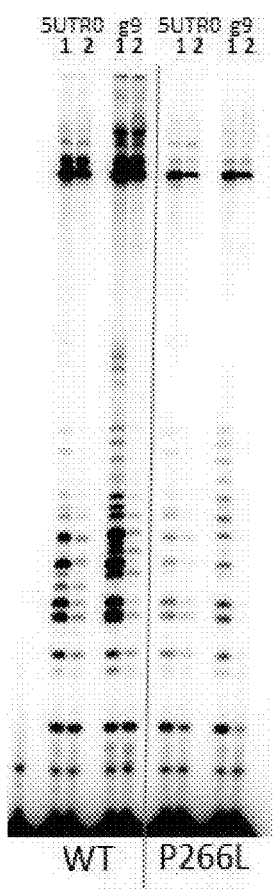
FIGS. 6A-6C show results from the IVT reactions described in Example 3.
Figure 6B:
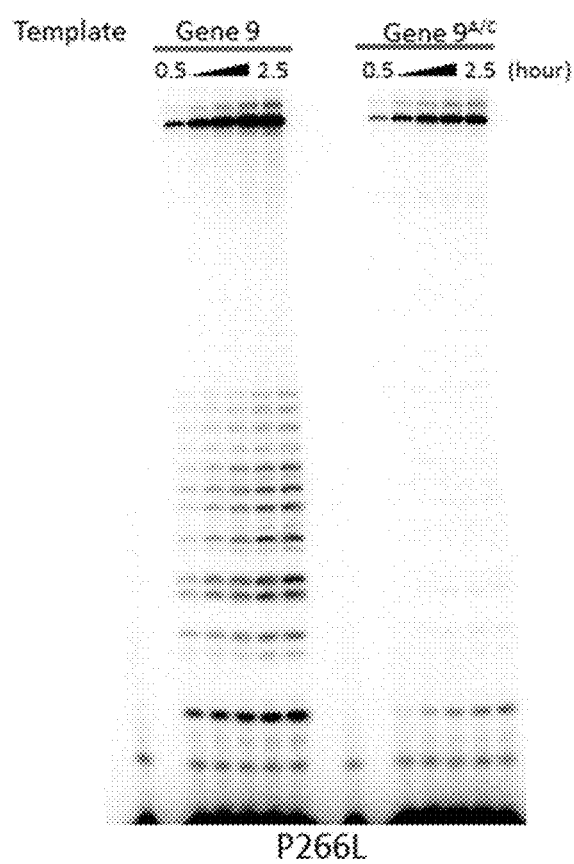
Figure 6C:
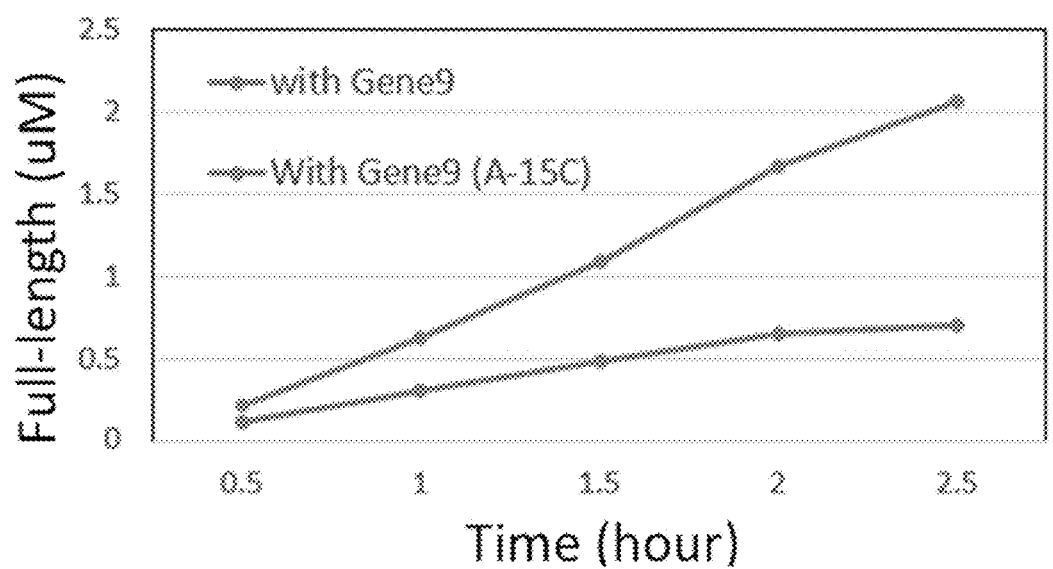

In vitro transcription (IVT) reactions were performed using constructs with the following combination of promoter and ITS: WT T7 promoter+5' UTR0 ITS; modified (A-15C) T7 promoter+5' UTR0 ITS; WT T7 promoter+Gene 9 ITS; or modified (A-15C) T7 promoter+Gene 9 ITS. Abortive: run-off ratio (Table 4) and yield of run-off product (Table 5) was assessed for each construct combined with either WT T7 polymerase or modified (P266L) T7 polymerase. Tables 4, 5, 6 and FIGS. 6A-6C show results from the IVT reactions.

TABLE 4

| | Abortive:Run-off Ratio | |
|---|---|---|
| Construct | wt | P266L* |
| 5UTR0 | 0.88:1 | 0.45:1 |
| 5UTR0$^{A/C}$ | 0.50:1 | 0.43:1 |
| Gene9 | 1.18:1 | 1.0:1 |
| Gene9$^{A/C}$ | 0.33:1 | 0.13:1 |

*For WT 250U/20 μL rxn, 37° C. for 30 min.
For P266L, 200U/20 μL rxn, 37° C. for 1 h.

TABLE 5

| | Run-off Product (μM) | |
|---|---|---|
| Construct | wt | P266L |
| 5UTR0 | 2.1 | 0.8 |
| 5UTR0$^{A/C}$ | 1.2 | 0.2 |
| Gene9 | 3.8 | 0.6 |
| Gene9$^{A/C}$ | 2.5 | 0.3 |

TABLE 6

| | Run-off Ratio by P266L | |
|---|---|---|
| Time | Gene 9 | Gene 9$^{A/C}$ |
| 0.5 h | 1.57:1 | 0.15:1 |
| 1 h | 1.14:1 | 0.13:1 |
| 1.5 h | 1.00:1 | 0.13:1 |
| 2 h | 0.92:1 | 0.13:1 |
| 2.5 h | 0.80:1 | 0.08:1 |

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a ribonucleic acid (RNA) of interest, the method comprising:
   (a) performing an in vitro transcription reaction using an initial amount of an in vitro transcription construct that comprises a modified T7 promoter operably linked to a nucleic acid that comprises a 5' untranslated region (UTR) and an open reading frame encoding the RNA of interest, wherein the modified T7 promoter comprises a point mutation at position −14, −15, and/or −16, relative to a wild-type T7 promoter that comprises the nucleotide sequence of SEQ ID NO: 18, and the 5' UTR comprises the T7 bacteriophage Gene 9 sequence of SEQ ID NO: 12; and
   (b) producing the RNA of interest.

2. The method of claim 1, wherein the ratio of truncated single-stranded RNA (ssRNA):full-length ssRNA produced from the in vitro transcription reaction is less than 1:1.

3. The method of claim 2, wherein the ratio of truncated ssRNA transcript:full-length ssRNA produced from the in vitro transcription reaction is 0.1:1 to 0.9:1.

4. The method of claim 1, wherein the amount of full-length single-stranded RNA produced from the in vitro transcription reaction is at least 15 times greater than the initial amount of the construct.

5. The method of claim 4, wherein the amount of full-length single-stranded RNA produced from the in vitro transcription reaction is 15 times to 100 times greater than the initial amount of the construct.

6. The method of claim 1, wherein the RNA of interest is a mRNA.

7. The method of claim 6, wherein the RNA of interest encodes a therapeutic protein or a prophylactic protein.

8. The method of claim 7, wherein the RNA encodes an antigen.

9. The method of claim 1, wherein the modified T7 promoter comprises an A to C point mutation at position −15, relative to a wild-type T7 promoter that comprises the nucleotide sequence of SEQ ID NO: 18.

10. The method of claim 1, wherein the modified T7 promoter comprises an T to C point mutation at position −14, relative to a wild-type T7 promoter that comprises the nucleotide sequence of SEQ ID NO: 18.

11. The method of claim 1, wherein the modified T7 promoter comprises an T to G point mutation at position −14, relative to a wild-type T7 promoter that comprises the nucleotide sequence of SEQ ID NO: 18.

12. The method of claim 1, wherein the modified T7 promoter comprises an A to G point mutation at position −15, relative to a wild-type T7 promoter that comprises the nucleotide sequence of SEQ ID NO: 18.

13. The method of claim 1, wherein the modified T7 promoter comprises an A to C point mutation at position −16, relative to a wild-type T7 promoter that comprises the nucleotide sequence of SEQ ID NO: 18.

14. The method of claim 1, wherein the modified T7 promoter comprises an A to G point mutation at position −16, relative to a wild-type T7 promoter that comprises the nucleotide sequence of SEQ ID NO: 18.

* * * * *

SEQUENCE LISTING

<160> NUMBER OF SEQ ID NOS: 29

<210> SEQ ID NO 1
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 1
cagaagctaa tacgactcac tatagggaaa taagagagaa aagaagagta agaagaaata    60
taagagccac catgggagtg cacgagtgtc    90

<210> SEQ ID NO 2
<211> LENGTH: 20
<212> TYPE: DNA

```
<213> ORGANISM: Artificial Sequence
<220> FEATURE:
<223> OTHER INFORMATION: Synthetic polynucleotide

<400> SEQUENCE: 2
ggagaacctt aaggtttaac                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gggacaatgc ttaaggtcgc                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
ggaggtacac accatgatgt                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
ggagacacta tatgtttcga                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
gggaagactc cctctgagaa                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
gggagaccac agcggtttcc                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
gagagagatt attgagaacg                                               20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
ggagacacac catgttcaaa                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
ggagatatta ccatgcgtga                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
gggagatagg ggcctttacg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
gggagacctc atctttgaaa                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
gggagaccac aacggtttcc                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
gggagaacaa tacgactacg                                               20

<210> SEQ ID NO 15
<211> LENGTH: 20
<212> TYPE: DNA
<213> ORGANISM: Artificial Sequence
<220> FEATURE:
```

<223> OTHER INFORMATION: Synthetic polynucleotide

<400> SEQUENCE: 15
gggagaggcg aaataatctt                                             20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
gggagaggag ggacgaaagg                                             20

<210> SEQ ID NO 17
<211> LENGTH: 90
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (45)..(71)
<223> OTHER INFORMATION: n is a, c, g, or t
<220> FEATURE:
<221> NAME/KEY: misc_feature
<222> LOCATION: (75)..(90)
<223> OTHER INFORMATION: n is a, c, g, or t

<400> SEQUENCE: 17
cagaagctaa tacgactcac tataggqaga cctcatcttt gaagnnnnnn nnnnnnnnnn  60
nnnnnnnnnn natgnnnnnn nnnnnnnnnn                                  90

<210> SEQ ID NO 18
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 18
taatacgact cactata                                                17

<210> SEQ ID NO 19
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 19
cagaagctaa tacgactcac tatagggaaa taagagagaa aaga                  44

<210> SEQ ID NO 20
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 20
cagaagctac tacgactcac tatagggaaa taagagagaa aaga                  44

<210> SEQ ID NO 21
<211> LENGTH: 44

```
<212> TYPE: DNA
<213> ORGANISM: Artificial Sequence
<220> FEATURE:
<223> OTHER INFORMATION: Synthetic polynucleotide

<400> SEQUENCE: 21
cagaagctaa tacgactcac tatagggaaa gaagagagaa aaga            44

<210> SEQ ID NO 22
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 22
cagaagctaa tacgactcac tatagggaga cctcatcttt gaag            44

<210> SEQ ID NO 23
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 23
cagaagctac tacgactcac tatagggaga cctcatcttt gaag            44

<210> SEQ ID NO 24
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 24
cagaagctaa tacgactcac tatagggaga ccacaacggt ttcc            44

<210> SEQ ID NO 25
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 25
cagaagctac tacgactcac tatagggaga ccacaacggt ttcc            44

<210> SEQ ID NO 26
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 26
cagaagctaa tacgactcac tatagggaga ggagggacga aagg            44

<210> SEQ ID NO 27
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 27
```

```
cagaagctac tacgactcac tatagggaga ggagggacga aagg              44

<210> SEQ ID NO 28
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 28
cagaagctaa tacgactcac aatcgcggag cctcatcttt gaag              44

<210> SEQ ID NO 29
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 29
cagaagctac tacgactcac aatcgcggag cctcatcttt gaag              44
```